United States Patent
Kawano

[11] Patent Number: 5,454,208
[45] Date of Patent: Oct. 3, 1995

[54] BAG FOR MEDICAL USE, METHOD AND APPARATUS FOR MANUFACTURING THE SAME

[75] Inventor: Takumi Kawano, Yokohama, Japan

[73] Assignee: Kawasumi Kagaku Kogyo Kabushiki Kaisha, Tokyo, Japan

[21] Appl. No.: 228,218

[22] Filed: Apr. 15, 1994

[30] Foreign Application Priority Data

Apr. 28, 1993 [JP] Japan .................... 5-125419

[51] Int. Cl.⁶ ............... B65B 1/02; B65B 1/06; B65B 57/18; B65B 61/00
[52] U.S. Cl. .......... 53/410; 53/412; 53/433; 53/451; 53/55; 53/511; 53/133.2; 53/140; 53/546; 53/551
[58] Field of Search ............ 53/410, 412, 433, 53/434, 451, 510, 140, 546, 551, 133.2, 55

[56] References Cited

U.S. PATENT DOCUMENTS

| | | | |
|---|---|---|---|
| 2,856,677 | 10/1958 | Rekettye | 53/133.2 X |
| 3,069,303 | 12/1962 | Scholle | 53/133.2 X |
| 3,251,915 | 5/1966 | Pechthold | 53/140 X |
| 3,331,902 | 7/1967 | Stark | 53/140 X |
| 3,812,572 | 5/1974 | Weikert | 53/133.2 X |
| 3,863,424 | 2/1975 | Naumann | 53/140 X |
| 4,132,051 | 1/1979 | Rausing | 53/140 X |
| 4,221,760 | 9/1980 | Mnilk et al. | 53/140 X |
| 4,695,337 | 9/1987 | Christine | 53/133.2 X |
| 4,721,453 | 1/1988 | Belanger, Jr. | 53/140 X |
| 5,272,855 | 12/1993 | Togi et al. | 53/133.2 X |

Primary Examiner—Horace M. Culver
Attorney, Agent, or Firm—Michael J. Striker

[57] ABSTRACT

The apparatus for manufacturing bags for medical use includes an extruding machine, a device for forming an extruded tube, a device for supplying outlet devices, and a device for conveying the extruded tube horizontally. The device for forming the extruded tube has a die through which pass a sterile air supply line, a medical fluid supply line, an air recovering line and a second sterile air supply line which passes through the medical fluid supply line. The extruding machine extrudes a tube in a fused state and outlet devices are welded to the extruded tube in the fused state. The extruded tube is pressed by the formation device at intervals along it to form fused portions bounding chambers and a fluid passage through each fused portion to connect the chambers. Sterile air is fed into the extruded tube and the shape of the extruded tube is maintained by the pressure of the sterile air. The volatile component contained in the component material used to make the bag is recovered by a recovering line connected with the interior of the tube. Also, a medical fluid is fed from the medical fluid supply line into the chambers. The fluid passages of the extruded tube thus filled with the medical fluid are sealed by a welding and cutting device, and, at the same time, the fused portions are cut through to form the individual bags.

20 Claims, 13 Drawing Sheets

FIG_1
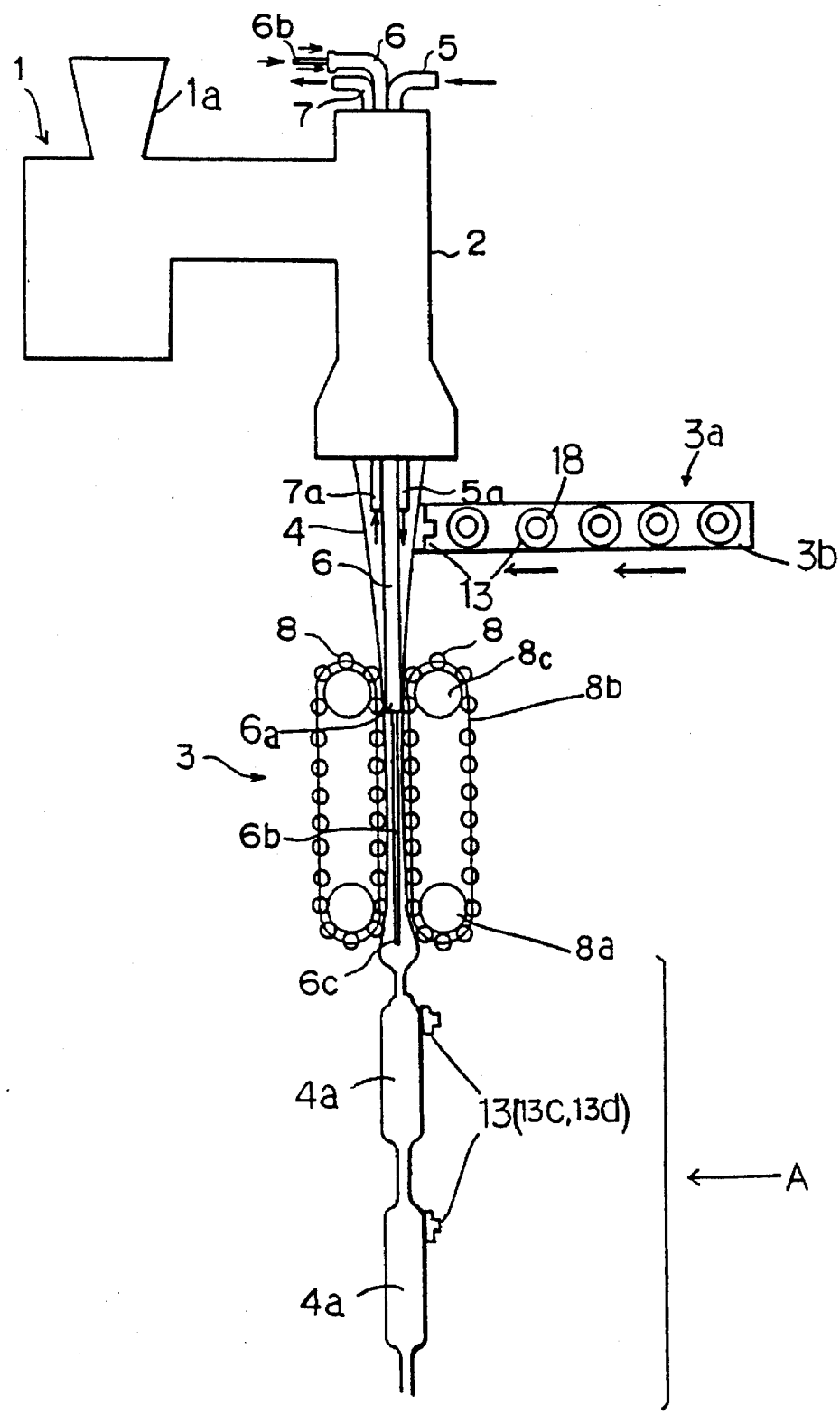

FIG_2
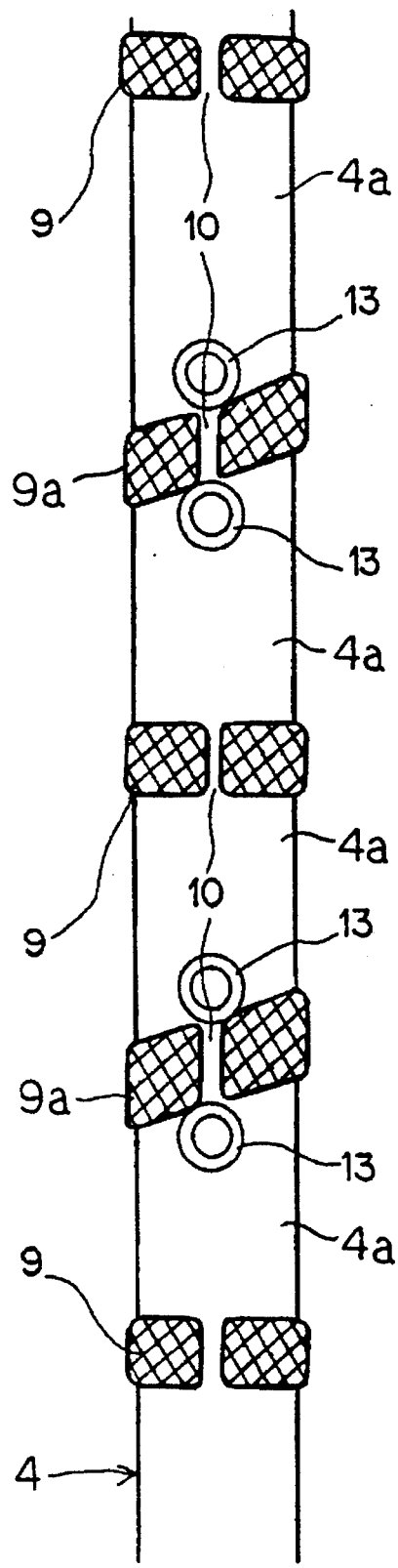

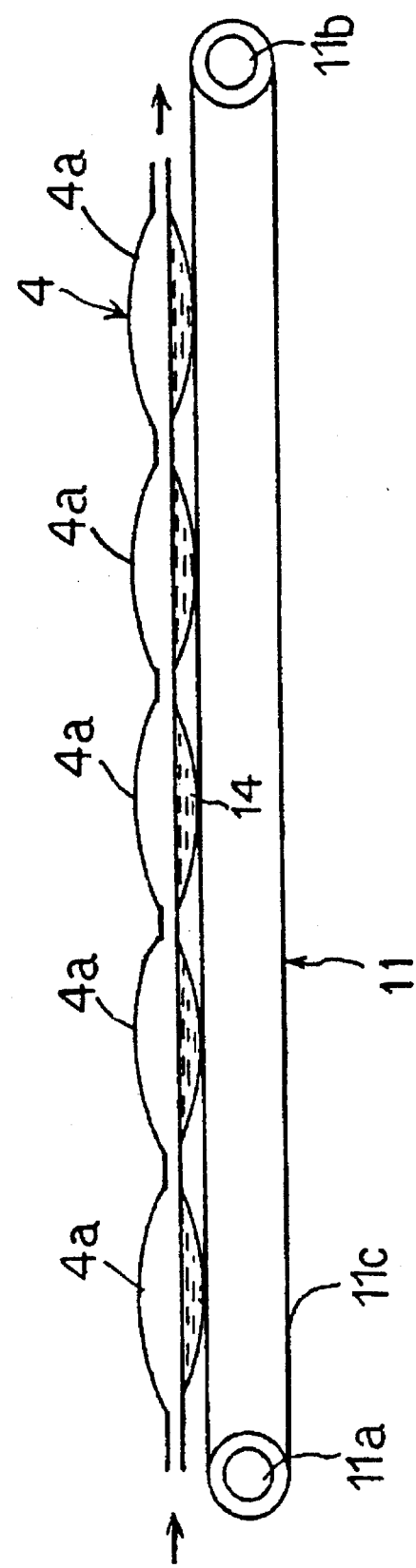

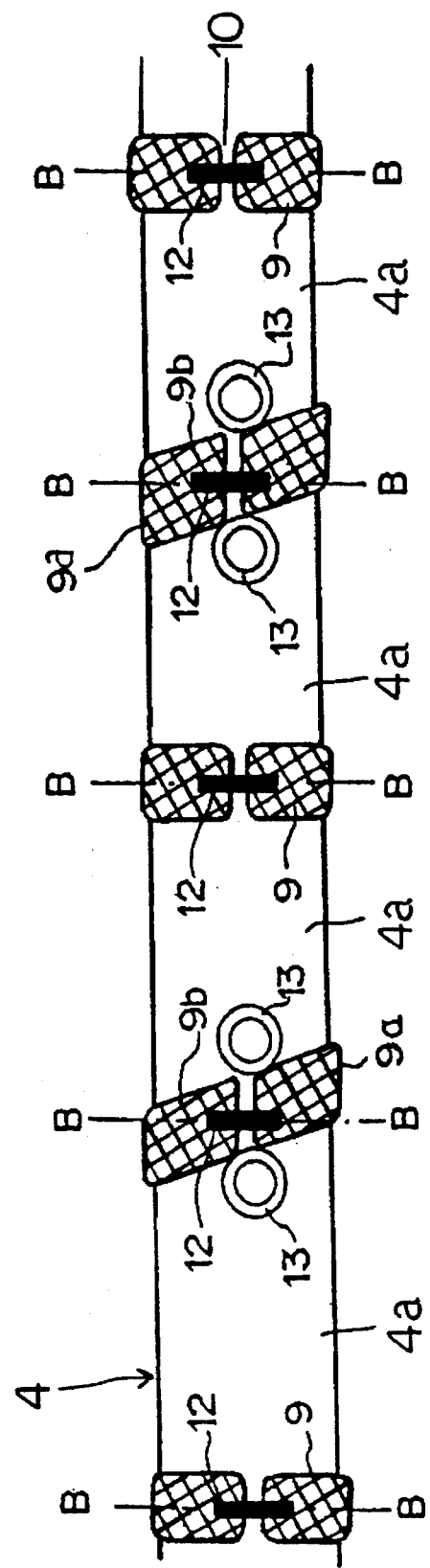
FIG._4

FIG_5
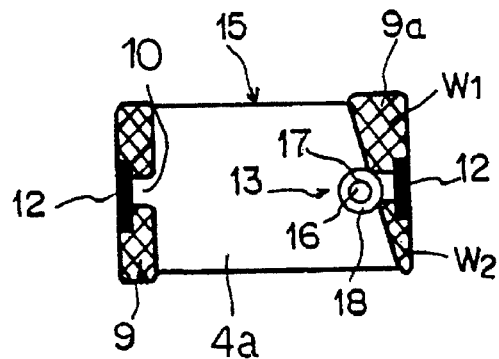
FIG_6
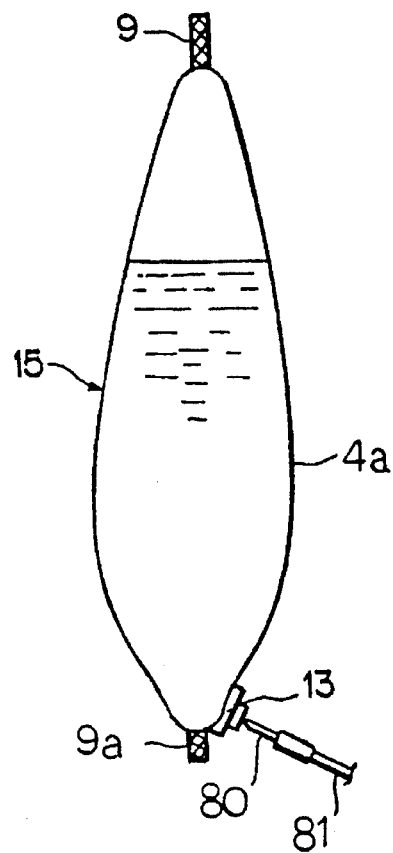

FIG_7
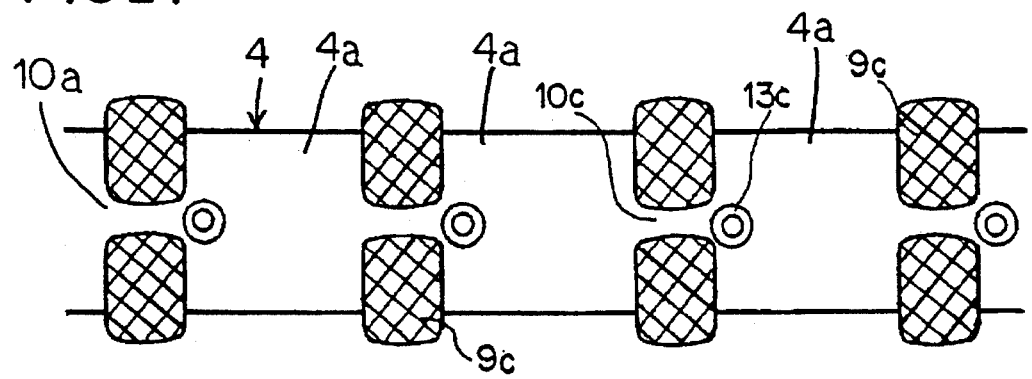
FIG_8
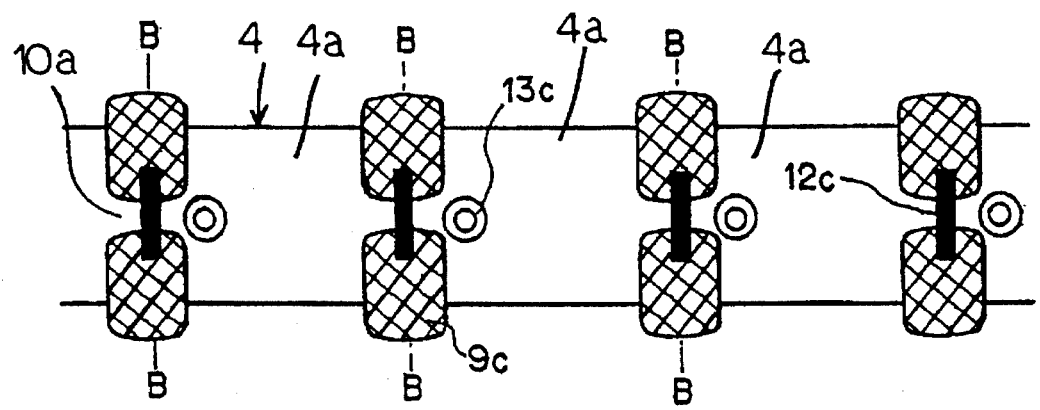
FIG_9
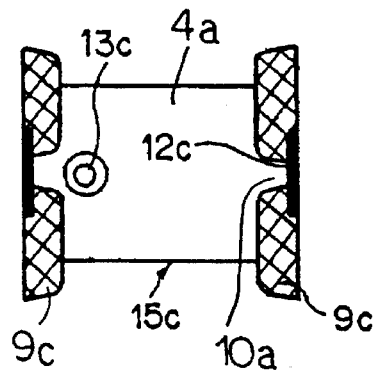

FIG_10
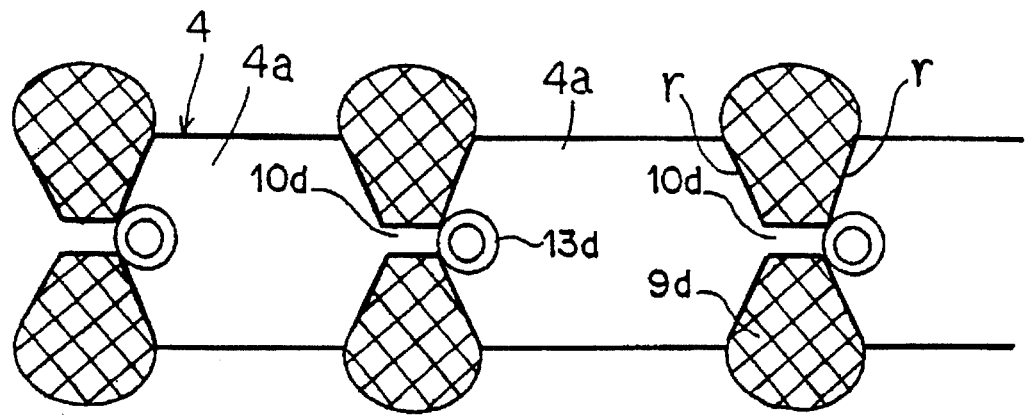
FIG_11
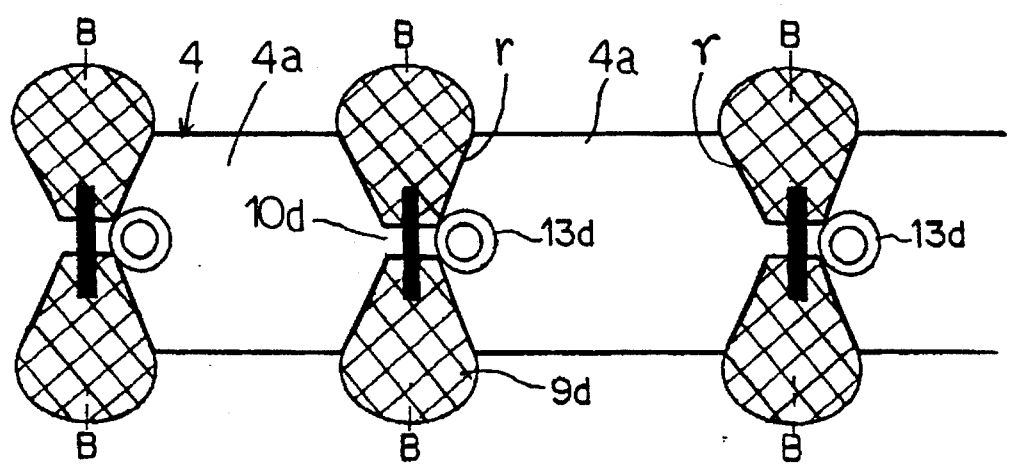
FIG_12
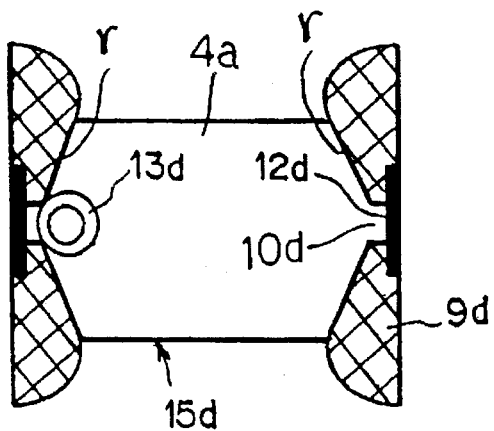

FIG_13
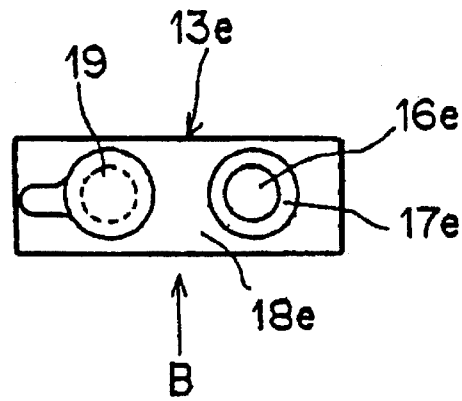
FIG_14
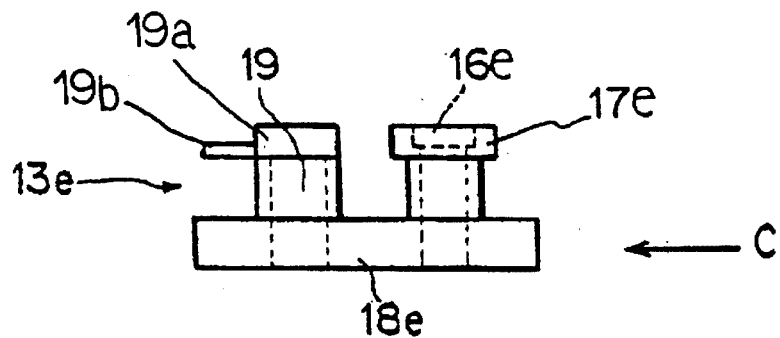
FIG_15
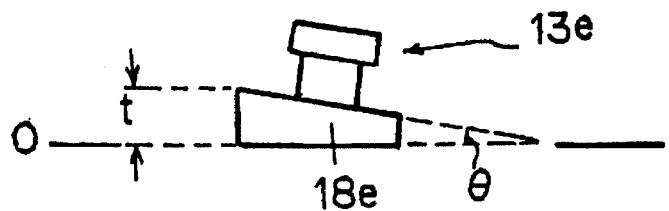

FIG_16
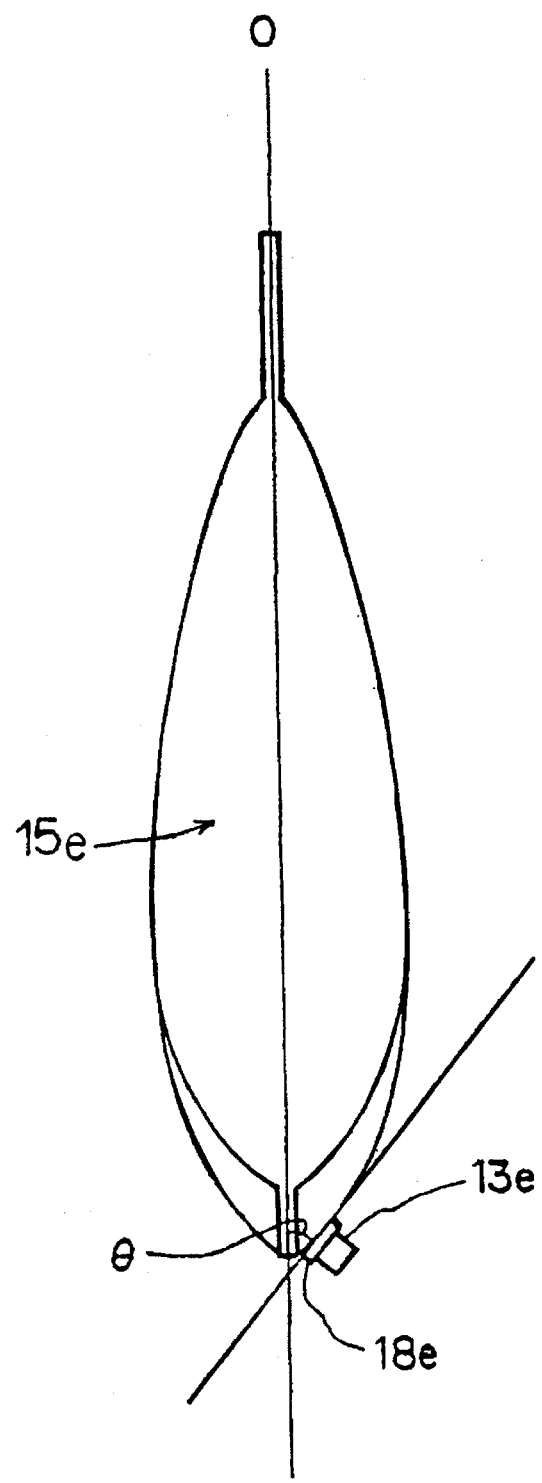

FIG_17
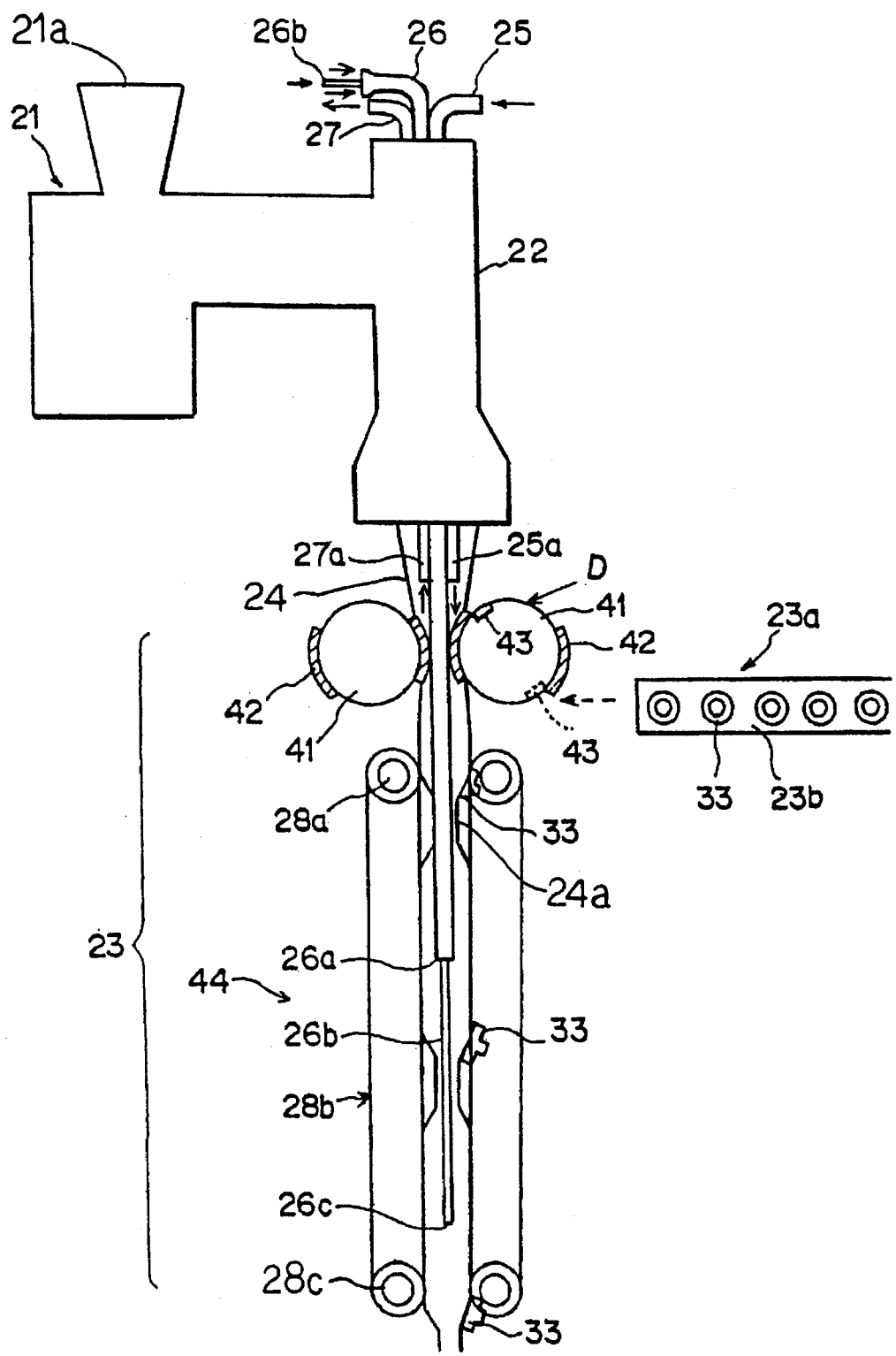

FIG_18
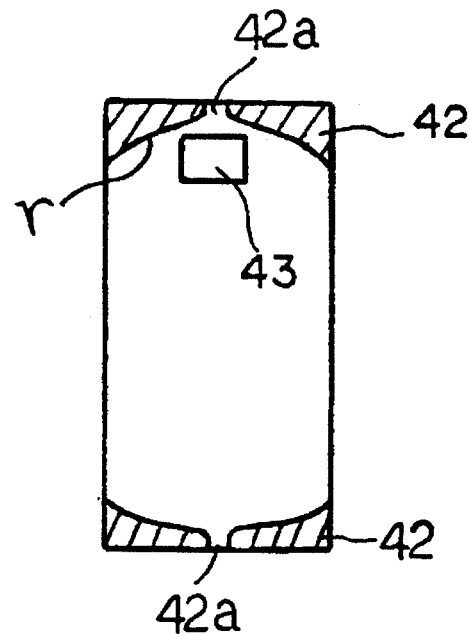
FIG_19
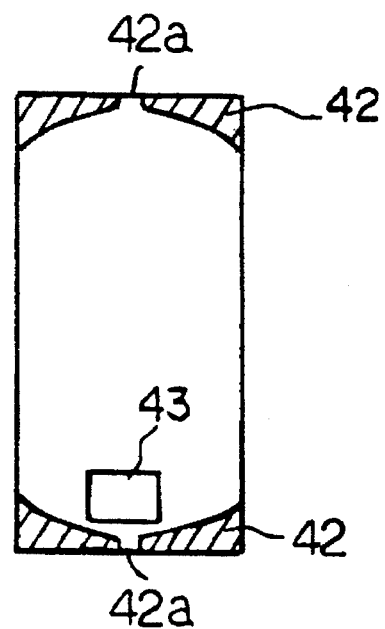

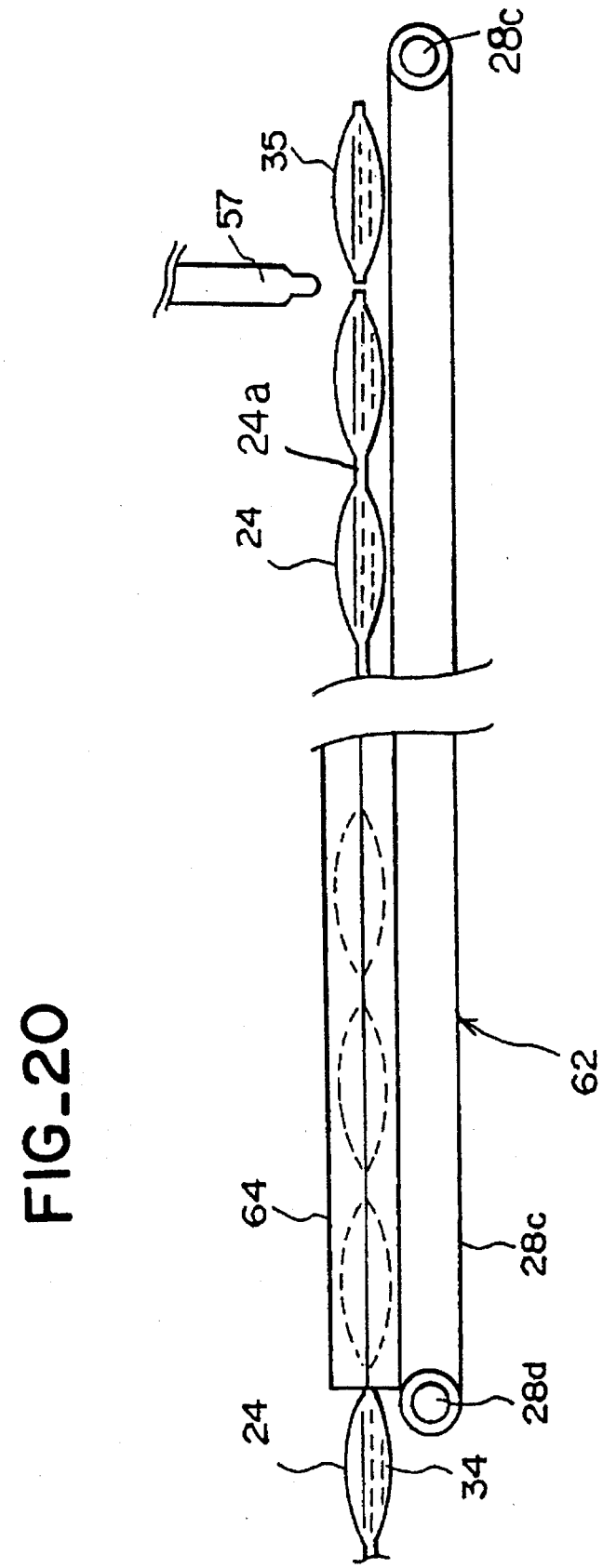

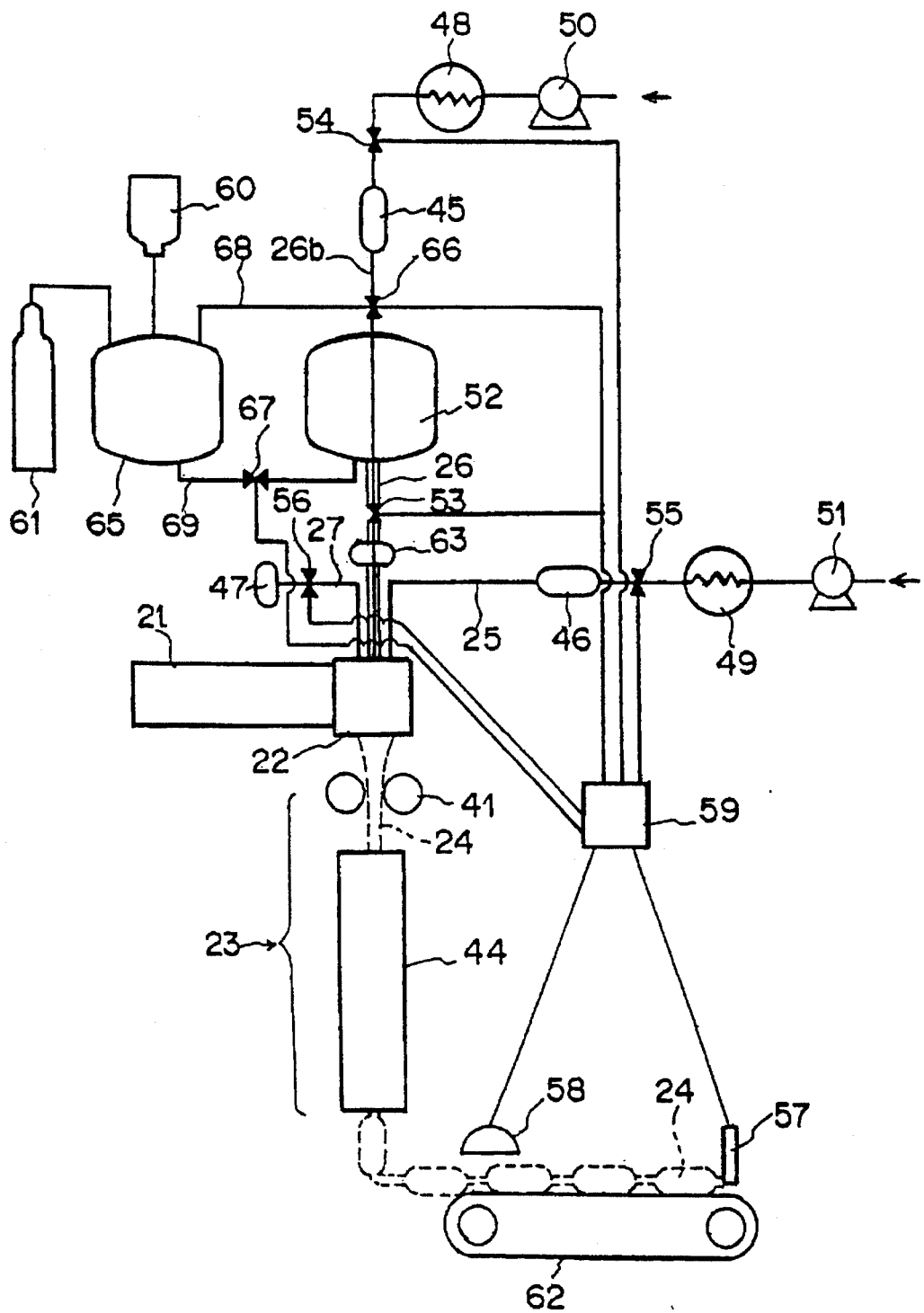
FIG_21

BAG FOR MEDICAL USE, METHOD AND APPARATUS FOR MANUFACTURING THE SAME

BACKGROUND OF THE INVENTION

1. Field of the Invention

The present invention relates to bags for medical use made of a flexible synthetic resin, such as bags for clysis, medical fluid, and blood, and also to a method and apparatus for manufacturing such bags. More particularly, the invention relates to the provision of a system or apparatus for continuously executing a series of manufacturing processes from the extrusion molding of a component material for the bag to the final product in which a medical fluid is filled under sterile and dustless conditions.

2. Prior Art

Bags for clysis, medical fluid, blood, and others for medical use have hitherto been manufactured in the following manner, for example:

(1) Two flexible synthetic resin sheets are superposed. The peripheral edges of the sheets are welded together while making outlet devices or mouths for clysis or the like between the ends of the sheets to form a bag for clysis.

(2) A tube made from a flexible synthetic resin is cut to a predetermined size. By making an outlet device for clysis or the like at either one or both ends of the tube, both of the open ends of the tube are welded to make a bag for clysis.

However, since the method involves welding separate sheets or open ends of a tube by making an outlet device or mouth according to these methods, the inner surface of the sheets or the tube (the inner surface of the bag main body) is exposed to the outside air. Hence there is a possibility that during exposure to the outside air, bacteria, fine-grains, fine particles, cut chips of the outlet device or mouth for clysis or the like adhere to the inner surface of the bag main body. This is not desirable from the standpoint of hygiene. Also, after the bag is formed for medical use, a medical fluid or the like is filled in it. As a result, the number of manufacturing process steps is inevitably increased. Also, there is a danger that the medical fluid or the interior of the bag is contaminated when the medical fluid is filled. Furthermore, in the prior art, a comparatively wide area of the sheets or the ends of the tube must be welded. Thus the power consumption during manufacturing of the bag is comparatively large, resulting in a disadvantage economically.

SUMMARY OF THE INVENTION

It is a first object of the present invention to provide a method and apparatus for making bags for medical use under completely sterile and dustless conditions in a series of manufacturing process steps from a step of extrusion molding of a component material to the making of the final product in which a medical fluid is filled without allowing any portions, particularly those portions corresponding to the inner surface of the bags, to be exposed to the outside air during manufacture.

It is a second object of the present invention to provide a method and apparatus for making bags for medical use capable of continuously and automatically forming an extruded tube, installing outlet devices, and filling a medical fluid, and also capable of implementing the rationalization, and the efficiency enhancement in the manufacturing processes of the bags for medical use.

It is a third object of the present invention to provide a highly economical method and apparatus for manufacturing bags for medical use with a comparatively less power consumption than the conventional methods.

It is a fourth object of the present invention to provide a method and apparatus for manufacturing bags for medical use in which the volatile component produced from the additives to the component material is recovered during manufacture so that the volatile component is not allowed to remain on the inner surface of the bags after making the finished products.

The purpose of the fourth object of the invention is to provide a hygienic method and apparatus for manufacturing bags for medical use, in which the outlet device for a connected or piercing needle can be welded easily and firmly to the outer surface portion of the chamber to fill in a solution to be drawn from the chamber, and to prevent adherence of any cut chips and the like from the outlet device on the inner surface of the bags.

It is a fifth object of the present invention to provide bags for medical use capable of providing a reliable smooth outflow of a medical fluid held in a chamber formed by fused portions of the bag in a desirable configuration at both ends of the chamber for receiving the solution to be drawn from the bag.

It is a sixth object of the present invention to provide bags for medical use, in which the lower aperture of the outlet device for a piercing or connected needle is blocked by the outer surface of the chamber portion thereby making it easy to open the bag just by puncturing the outer surface of the chamber with a needle.

A manufacturing method of the present invention according to a typical embodiment comprises the following steps of:

forming an extruded tube of a material for the bags for medical use in a fused state by extrusion;

heating outlet devices for the bags and contacting the heated outlet devices to the outer surface of the extruded tube in the fused state to weld the outlet devices to the outer surface of the tube;

forming fused portions of the extruded tube spaced from each other by pressing the aforesaid extruded tube at intervals along it in the longitudinal direction to form a plurality of chambers for a medical fluid while providing fluid passages in the fused portions to connect the chambers for passage of the medical fluid;

supplying a medical fluid to the chambers through the fluid passages; and sealing the fluid passages of the fused portions of the extruded tube in an air-tight manner after injecting the medical fluid and cutting the fused portions in a width or transverse direction across the extruded tube and across the sealed fluid passages to form the bags containing the medical fluid.

An apparatus for executing the above-mentioned manufacturing method comprises:

means for forming an extruded tube of a material for the bags for medical use in a fused state by extrusion;

means for heating outlet devices for the bags and means for contacting the heated outlet devices to the outer surface of the extruded tube in the fused state to weld the outlet devices to the outer surface of the tube;

means for forming fused portions of the extruded tube spaced from each other by pressing the aforesaid extruded tube at intervals along it in the longitudinal direction to form a plurality of chambers for a medical fluid while providing fluid passages in the fused portions to connect the chambers for passage of the medical fluid;

means for supplying a medical fluid to the chambers through the fluid passages; and means for sealing the fluid passages of the fused portions of the extruded tube in an air-tight manner after injecting the medical fluid and means for cutting the fused portions in a width or transverse direction across the extruded tube and across the sealed fluid passages to form the bags containing the medical fluid.

According to one embodiment of the apparatus of the present invention, means for supplying a sterile air into the aforesaid extruded tube is also provided. An air collection line for collecting air in the extruded tube is also provided.

A flexible bag for medical use manufactured by the above-mentioned method and apparatus includes fused portions formed at both ends of the bag to bound a chamber for a medical fluid; and an outlet device welded on the outer surface portion of the chamber.

Each outlet device advantageously comprises a cylindrical body provided with a lower opening blocked by the outer surface of the chamber.

According to one embodiment of the present invention, at least one side of the fused portions is formed at a predetermined angle to the transverse direction of the bag, and an outlet device is welded to the tube in the vicinity of the narrower part of the fused portion.

BRIEF DESCRIPTION OF THE DRAWING

The objects, features and advantages of the present invention will now be illustrated in more detail by the following detailed description, reference being made to the accompanying drawing in which:

FIG. 1 is a schematic plan view of an apparatus for manufacturing bags for medical use according to the present invention;

FIG. 2 is a schematic plan view of an extruded tube after its formation by the apparatus of FIG. 1 as in the direction indicated by the arrow A in FIG. 1;

FIG. 3 is a schematic side view of a step of a process for making the bags in which a medical fluid is being filled in the extruded tube;

FIG. 4 is a schematic side view of a step of a process for making the bags in which the fluid passages formed in the fused portions of the extruded tube are sealed and the fused portions are cut transversely;

FIG. 5 is a schematic plan view of a bag for medical use according to the present invention;

FIG. 6 is a schematic cross-sectional view of a bag for medical use according to the present invention in use;

FIG. 7 is a schematic plan view showing the configuration of an extruded tube after its formation according to a second embodiment of the method of the present invention;

FIG. 8 is a schematic plan view of the extruded tube shown in FIG. 7 after the fluid passages formed in the fused portions are sealed and the position B where the fused portions are cut transversely;

FIG. 9 is a schematic plan view of a bag for medical use manufactured with the extruded tube according to the second embodiment;

FIG. 10 is a schematic plan view showing the configuration of an extruded tube after its formation according to a third embodiment of the method of the present invention;

FIG. 11 is a schematic plan illustrating the sealing of the fluid passages in the fused portions of the extruded tube according to a third embodiment of the invention and the position B where the fused portions are cut transversely;

FIG. 12 is a schematic plan view of a bag for medical use manufactured with the extruded tube according to the third embodiment of the method;

FIG. 13 is a schematic plan view of another embodiment of the outlet devices according to the present invention;

FIG. 14 is a schematic side view of the device shown in FIG. 13 observed in the direction indicated by the arrow B in FIG. 13;

FIG. 15 is a schematic side view of the device of FIG. 13 in the direction indicated by the arrow C in FIG. 14;

FIG. 16 is a schematic side view showing an embodiment of the bag in which an outlet device is attached to the bag main body;

FIG. 17 is a schematic plan view of a second embodiment of an apparatus for manufacturing bags for medical use according to the present invention;

FIG. 18 is a schematic front view of a pressing roller in the apparatus for manufacturing bags for medical use according to the second embodiment as seen in the direction indicated by the arrow D in FIG. 17;

FIG. 19 is a schematic rear view of the apparatus illustrated in FIG. 18;

FIG. 20 is a schematic side view of a step of a process according to the invention in which the extruded tube of the present invention is being transported horizontally; and FIG. 21 is a schematic view showing a system including devices for supplying sterile air, supplying a medical fluid, recovering the air, and detecting liquid leakage in the apparatus for manufacturing bags for medical use according to the present invention.

DETAILED DESCRIPTION OF THE PREFERRED EMBODIMENTS

FIG. 1 shows an apparatus for manufacturing bags for medical use according to the present invention. This apparatus comprises an extruding machine 1, a die 2 for extruding a tube (hereinafter referred to as die 2), a device 3 for forming the tube, and a device 3a for applying outlet devices 13 to the tube.

The extruding machine 1 is a standard extruding machine in which the plastic starting material put in from a hopper 1a is softened by heat and extruded continuously from a die 2. In the die 2, a line 5 for supplying a sterile air, a line 6 for supplying a medical fluid, and a line 7 for withdrawing air are inserted through the rear side of the die 2. The nozzle 5a for the sterile air supply line 5, nozzle 7a for the air return and the medical fluid supply line 6 is arranged so that it is extends or protrudes from the nozzle of the die 2. Also, the nozzle 6a of the medical fluid supply line 6 is extended to the entrance zone of the device 3 for forming the extruded tube. Furthermore, a second line 6b provide with a nozzle 6c for supplying sterile air is inserted through the interior of the medical fluid supply line 6. This nozzle 6c is positioned in the exit zone of the device 3 for forming the tube.

The device 3a for supplying the outlet devices is arranged in the vicinity of the exit of the die 2. It comprises a hot plate 3b which carries the outlet devices 13 in the direction of the extruded tube 4. The hot plate 3b has a heating device to heat the upper surface thereof to a given temperature. Thus the parts of the outlet devices 13 mounted on the upper surface of the hot plate 3b, which are to be contacted with the extruded tube, that is, the bottom flanges 18 of the outlet devices 13 in the present embodiment (refer to the description in conjunction with FIG. 5), are heated and maintained at a high temperature. It is sufficient when the temperature of the bottom flanges is high enough so that the flanges 18 and the extruded tube 4 which is maintained in a fused state will be welded to each other on contact.

For the mechanism of the device 3a for supplying the outlet devices 13, any arbitrary mechanism such as a mechanism by which the hot plate 3b is rotated endlessly and one by which the outlet devices 13 are applied one after another by extension of a protruding element carrying them in the direction of the tube 4 can be used. Also, a mechanism to press the outlet devices 13 and install them on the tube 4 can be used. This mechanism, for example, can be a mechanism in which each of the outlet devices 13 carried to the tip end of the hot plate 3b is clamped, and then, the bottom end of the outlet device bottom flange 18 is pushed toward the tube 4, or it can be a mechanism in which a reversing guide is provided so that the bottom flange 18 of the outlet device 13 positioned at the tip end of the hot plate 3b faces the extruded tube 4 and the reversed outlet device 13 is pressed to the extruded tube 4.

The device 3 for forming the tube is provided with two forming means each of which includes a driving shaft 8a, a driven shaft 8c and a conveyer element 8b passing around these shafts. Rollers 8 are spaced at intervals from each other on the conveyor element 8b. This device 3 for forming the tube comprises a pair of the forming means, each of the forming means being arranged on either the left-hand or right-hand sides of the tube 4. The intervals between adjacent rollers 8 are usually equal to each other. However, if several kinds of bags having different capacities are to be manufactured at the same time, different intervals may be set between adjacent rollers 8.

In the apparatus shown in FIG. 1, rollers for carrying the extruded tube are also included on the conveyer element 8b. The rollers 8 provided for forming the extruded tube 4 have a diameter greater than those of the carrier rollers. The rollers 8 are only a portion of the rollers on the conveyor element 8b since the carrier rollers are also included there.

A slit is formed in the central part of the surface of each of the rollers 8 so that fluid passages 10 are formed in the fused portions when the extruded tube 4 has been welded by pressing it with the rollers 8 as described later.

Also, the slits serve as a release or escape so that the sterile air supply line 6b does not interfere with the rollers 8 when left and right rollers 8 are pressed together to form the fused portion.

When a synthetic resin material for bags for medical use is put in the hopper 1a of the extruding machine 1, the synthetic resin material passes through the die 2 after being heated and fused. It is extruded in a tubular form from the nozzle of the die 2. The outlet devices 13 supplied from the outlet device supply device 3a are applied to the outer surface of the extruded tube 4 in the fused state. The bottom flanges 18 of the outlet devices 13 are maintained at a high temperature. The bottom ends of the bottom flanges 18 are welded to the outer surface of the extruded tube 4 in the fused state when the bottom ends of the flanges are contacted with the tube 4. The position in which the outlet devices 13 are installed on the extruded tube 4 can be arbitrarily changed by modifying the supply position of the outlet device supply device 3a.

Then the extruded tube 4 on which the outlet devices 13 are applied is transported to the formation device 3. In the formation device or means for forming 3, the extruded tube 4 is pressed by pairs of the rollers 8 from the left-hand and right-hand sides to form the fused portions. As shown in FIG. 2, the fused portions 9 and 9a are provided with throughgoing fluid passages 10 in their central parts and are spaced at intervals in the longitudinal direction along the tube. In the present embodiment, first fused portions 9 which are substantially at right angles to the central axis of the extruded tube 4 and second fused portions 9a which are at a predetermined angle to the central axis of tube are formed alternately in series in the longitudinally direction along the tube 4, i.e. the closest adjacent fused portions to each of the first fused portions 9 are second fused portions 9b. In order to form the second fused portions 9a, it is preferable that the configuration of the die 2 for the rollers 8 is modified or the rotational shaft of the rollers 8 is inclined to the advancing direction of the conveyer element 8b when installed.

In this way, the fused portions 9 and 9a are formed by the formation device 3 on the extruded tube 4 at predetermined intervals along the tube 4. Thereby the chambers 4a for filling a medical fluid are formed in the longitudinal direction of the extruded tube 4.

The sterile air is fed to the extruded tube 4 under a given pressure from the sterile air supply line 5. As a result, the extruded tube 4 can be maintained in an inflated shape at the time of installation of the outlet devices 13 on the tube and of passing if the tube through the formation device 3. Also, the air fed into the extruded tube 4 is withdrawn through the air recovering line 7. Therefore, the volatile component of the additives, such as a plasticizer which can be evaporated (vaporization) from the extruded tube 4 at high temperature, is withdrawn or sucked out of the tube interior by the air recovering line 7. As a result, no volatile component remains and adheres to the inner surface of the extruded tube 4, thus maintaining its desirable hygienic condition.

The extruded tube 4 is pressed by the roller groups in the vicinity of the entrance of the formation device 3. Became the inner space comes to narrow (a narrow passage) the sterile air introduced from the nozzle 5a of the sterile air supply line 5 is bounced on the inner wall face of the extruded tube 4 in the vicinity of the narrow passage section. Hence, through the nozzle 7a, the air is exhausted to the outside by the recovering line 7.

The extruded tube 4 is conveyed on the horizontal carrier 11 as shown in FIG. 3 for filling with a medical fluid after passing through the formation device 3. The horizontal carrier 11 comprises a driving shaft 11a, a driven shaft 11b, and a conveyer element 11c passing around these shafts. After passing the formation device 3, guide mechanisms which are not illustrated in the drawing change the direction of travel of the extruded tube 4 to the horizontal direction. Then the extruded tube 4 is conveyed on the conveyer 11c horizontally.

The medical fluid to be filled in the bags for medical use is introduced from the medical fluid supply line 6 inserted from the rear side of the die 2 into the interior of the extruded tube 4 through the nozzle 6a. The medical fluid passes through the fluid passages 10 in the fused portions 9 and 9a formed in the extruded tube 4. The medical fluid is supplied to each of the chambers 4a of the extruded tube 4 moving in a horizontal state on the carrier 11. The nozzle 6a of the medical fluid supply line 6 is always positioned higher than the level of the medical fluid in the portion of the extruded tube 4 oriented in the horizontal state, thus making it possible to fill the medical fluid fully in each of the chambers 4a of the extruded tube 4 during the carrying on the carrier 11. Also, it is possible to inject a required amount of sterile air in each of the chambers 4a through the nozzle 6 of the sterile air supply line 6b. In this respect, since the fluid passages 10 of the fused portions 9 and 9a are sealed by a welding and cutting device which will be described detail later, there is no possibility that the medical fluid and the sterile air flow out from the tip end of the extruded tube 4 to the outside.

The medical fluid supply line 6 passes through the interior of the die 2. Therefore, when the medical fluid passes through the die 2, there is some danger that the medical fluid is bumped or changes its quality due to a sudden rise in the temperature. To avoid this, it is preferable to heat the medical fluid to a given temperature in advance before allowing it to pass through the interior of the die 2 or cool it after it is heated once.

The drawing speed of the extruded tube 4 from the die 2 can be set freely by an interlocking control of a controller or controlling means (not shown) for the driving speeds of the conveyer elements 8b of the formation device 3 and the conveyer element 11c of the carrier 11.

The extruded tube 4 whose chambers 4a is filled with the medical fluid is carried to the welding and cutting device (not shown in the present embodiment), and as shown in FIG. 4, the fluid passages 10 of the fused portions 9 and 9a are sealed by welding. The central parts of the fused portions 9 and 9a which include the welded portions 12 are cut in a right angle direction to the central axis of the extruded tube (to be cut along the line B—B in FIG. 4). In the welding and cutting device, a sealer or sealing means for sealing or welding closed the fluid passages 10 and a cutter to cut the fused portions 9 and 9a may be arranged separately from each other, or it may be well that the welding and cutting are performed at the same time by a marline used for both welding and cutting.

FIG. 5 shows an example of the bag for medical use which is obtained by the above-mentioned method of manufacture and the apparatus. The bag 15 for medical use is formed with a first fused portion 9 at one end of the chamber 4a and a second fused portion 9a at the other end. In the vicinity of the second fused portion 9a, a outlet device 13 is welded on the outer surface of the chamber 4a. The second fused portion 9a of the chamber 4a is inclined to the transverse direction of the bag and has a wider section w1 and a narrower section w2.

The outlet device 13 is made of a hard resin material and the entire body of it is formed in a protruding shape. In concretely, a flange 18 is formed at the bottom of a cylinder 17 having apertures on both ends. A rubber plug 16 is fitted in the upper end aperture or opening of the cylinder 17. The lower aperture or opening of the cylinder is formed in the bottom flange 18. This lower aperture or opening is closed in a water-tight manner by the outer surface of the chamber 4a for filling the medical fluid.

FIG. 6 shows the above-mentioned bag 15 for medical use in use. The needle 80 of a clysis device pierces the rubber plug 16 of the outlet device 13 installed on the lower end of the outer surface of the chamber 4a. For example the tip of the inserted needle 80 pierces the outer surface of the chamber 4a and extends into the interior of the chamber, thus injecting the medical fluid in the chamber into the body of a patient through the conductive tube 81.

Since the material used to make the bag 15 for medical use is flexible, the bottom part of the bag is expanded by the deadweight of the medical fluid in the chamber 4a. As a result, the outer surface of the bag near the second fused portion 9a is convex. Moreover, since the flow of the medical fluid is directed in a direction from the wider section w1 to the narrower section w2 in the vicinity of the second fused portion 9a, the medical fluid in the bag flows smoothly from the tip of the piercing needle 80 so that no medical fluid remains in it. Therefore, it is preferable to arrange the outlet device 13 as closely as possible to the narrower section w2 of the second fused portion 9a.

FIG. 7 shows an embodiment in which all the fused portions 9c of the extruded tube 4 are the same as the first fused portion 9 mentioned above. According to this embodiment, all the rollers 8 of the device 3 for forming the extruded tube have the same shape. Thus the roller die can have a simple structure and is provided with the fluid passage 10a in its central part so that the cost of roller manufacture is comparatively low.

The fluid passages 10a of the fused portions 9c of the aforesaid extruded tube 4 are sealed as shown in FIG. 8 by the welding and cutting device arranged on the horizontal carrier 11 as described earlier and are cut along the line B—B. In this way, a bag 15c for medical use shown in FIG. 9 is manufactured. For the bag 15c for medical use, fused portions 9c having the same configuration and/or shape extend in the transverse direction on both ends of the chamber 4a. The outlet device 13c is installed on the outer surface of the bag in the vicinity of one end and of one of the fused portions. According to this embodiment, too, the bottom part of the chamber having the outlet device 13c is outwardly curved or convex due to the deadweight of the medical fluid when the bag 15c is suspended and put into use, so that the medical fluid flows smoothly or is dispensed from the outlet device 13c.

FIG. 10 to FIG. 12 show another embodiment having different fused portions formed on the extruded tube 4. The fused portion 9d has a curved portion r which is recessed toward the fluid passage 10d formed in the central part of the fused portion 9d. The outlet device 13d is installed in the vicinity of the fluid passage 10d.

The fluid passages 10d in the aforesaid fused portions 9d of the extruded tube as shown in FIG. 11 are sealed in the same way as mentioned above and are cut through along the lines B—B of FIG. 11. In this way, the bag 15d for medical use which is shown in FIG. 12 is manufactured.

The curved portions r are located in the interior of the chamber 4a or on the side of the chamber 4a on the fused portions 9d formed on both ends of the chamber 4a of this bag 15d for medical use. A outlet device 13d is installed on the most recessed part of the curved portion r on the outer surface of the chamber.

Because of this structure for the fused portion 9d, the flow of the medical fluid filled in the chamber is directed in a direction toward the outlet device 13d along the curved portion r, hence making it possible for the medical fluid to smoothly flow from the piercing needle or the like connected to the outlet device 13d.

The apparatus for manufacture and the method thereof for the embodiment shown in FIG. 7 to FIG. 9 and the embodiment shown in FIG. 10 to FIG. 12 are only different in the means and method for forming the fused portions 9c and 9d of the extruded tube 4, and are the same as those shown in FIG. 1 and FIG. 3 in other aspects.

The configuration of the fused portions, the interval between the fused portions and other elements of the extruded tube 4 can be modified arbitrarily by changing the shape of the surface die for the rollers 8 of the aforesaid formation device 3, the arrangement of the rollers 8, and others characteristic features of the rollers 8. Also, the outlet device 13 can be installed at any position arbitrarily on the outer surface of the bag such as on the front, side, or other part thereof. The installation position of the outlet device 13 can be changed by adjusting the installation position of the outlet device supply device 3a and the timing of the outlet device supply among others. In the case where the outlet device is installed on both sides of the extruded tube 4, the outlet device supply device 3a may be arranged in the direction toward both sides of the extruded tube 4.

The structure of the outlet devices 13, 13c, and 13d are changeable according to the way of use and the like of the bag for medical use.

FIG. 13 to FIG. 15 show an outlet device in still another embodiment of the invention. A needle piercable outlet device 17e, a needle connecting outlet device 19 and a bottom flange 18e are all integral parts of this outlet device 13e. A rubber plug 16e is fitted into the upper aperture of a cylinder which is part of the needle piercable outlet device 17e. A cap 19a having a handle 19b covers the upper aperture of another cylinder comprising the needle connecting outlet device 19. The lower end parts of the cylinders which are part of the sticking needle outlet device 17e and the needle connecting outlet device 19 respectively are both opened at the bottom flange 18e. A plastic connecting needle fits into the needle connecting outlet device 19 and can be inserted therein when the cap 19a is removed. A metal needle can be stuck into the rubber plug 16e of the sticking needle outlet device 17e.

As shown in FIG. 15, the outer surface of the bottom flange 18e is arranged at an angle of inclination θ to its bottom surface in the transverse direction across the bottom flange 18e, i.e. in the direction B shown in FIG. 13. The angle of inclination θ should preferably be set at 30° to 45° to the center line O of the bag 15e as shown in FIG. 15 and FIG. 16. If the angle is less than 30°, the angle formed by the needle of a clysis device, stuck into or connected with the outlet device 13e and the bag 15e becomes almost vertical, thus making it difficult for the needle to remain inserted or connected. Also, if the angle is more than 45°, the angle formed by the needle and the bag 15e for medical use becomes almost horizontal, thus there is a possibility that the needle pierces the wall surface of the bag opposite to it.

By forming an angle of inclination θ of the outer surface of the bottom flange 18e in the manner mentioned above, the needle can be inserted or connected easily, and the medical fluid in the interior of the bag can smoothly flow from it.

In this respect, it is possible in a similar manner to provide an angle of inclination θ for the above-mentioned outlet devices 13, 13c, and 13d.

FIG. 17 is a view showing another embodiment of an apparatus for manufacturing bags for medical use according to the present invention. The apparatus comprises an extruding machine 21, a die 22, a device 23 for forming an extruded tube and a device 23a for supplying outlet devices 33. Similar to the embodiment in FIG. 1, a sterile air supply line 25, a medical fluid supply line 26 and an air recovering or return line 27 are inserted through a rear part of the die 22. Each of the nozzles 25a and 27a of the sterile air supply line 25 and the air recovering line 27 are arranged so that these nozzles protrude from the die 22. Also, the nozzle 26a of the medical fluid supply line 26 is extended into the interior of the device 23 for forming the extruded tube. A second sterile air supply line 26b passes through the interior of the medical fluid supply line 26. A nozzle 26c for this line is extended to the exit zone of the device 23 for forming the extruded tube.

The device 23a for supplying outlet devices has a hot plate 23b as in the first embodiment shown in FIG. 1, which carries the outlet devices 33 in the direction of the extruded tube 24. The bottom of each outlet device 33 mounted on the hot plate 23b is maintained at a high temperature.

The device 23 for forming the extruded tube has pressing rollers 41 provided with pressing portions 42 for the extruded tube 24 and a conveyor 44 for the tube 24. Installation grooves 43 are provided in the pressing portions 42 of the pressing rollers 41 for the outlet devices 33 as shown in FIG. 18 and FIG. 19. In the central part of the pressing portion 42, slits 42a are provided for forming fluid passages. The pressing portions 42 have curved parts on both edges thereof, respectively. By changing the configuration of the pressed portions 42 arbitrarily, it is possible to change the configuration of the fused portions formed on the extruded tube 24. Also, the configuration of the outlet device installation grooves 43 can be changed in accordance with the configuration of the outlet device 33.

The device 44 for conveying the extruded tube comprises a driving shaft 28a, a driven shaft 28c, and a conveyer element 28b passing around and installed between these shafts. The extruded tube 24 is conveyed downward while being pressed by the conveyer element 28b. In this respect, although not shown in detail in FIG. 17, the conveyer element 28b is structured so that it does not interfere with the outlet devices 33 installed on the extruded tube 24.

When a synthetic resin material is put into the hopper 21a of the extruding machine 21, the resin material is heated and fused, and then, extruded from the nozzle of the die 22 in a tubular form to form tube 24. The extruded tube 24 in the fused state is then pressed by the pressuring portions 42 of the rollers 41 in order to form the fused portions 24a. Also, the bottom flange of the outlet device 33 installed in the outlet device installation portion 43 contacts the outer surface of the extruded tube 24 in the fused state, and thus is welded to the tube 24. In this embodiment, the pressing of the extruded tube 24 and the welding of the outlet device 33 are performed alternately.

When the outlet device 33 mounted on the hot plate 23b is engaged in the outlet device installation groove 43 of the roller 41, the installation is performed automatically by an installation device which is not shown, but it can also be performed manually. If the configuration shown in FIG. 18 and FIG. 19 is adopted for the roller pressing portion 42, the welded portion 24a has the same shape as that shown in FIG. 10.

The extruded tube 24 is then carried to the horizontal carrier 62 shown in FIG. 20. The horizontal carrier 62 comprises a driving shaft 28d, a driven shaft 28c, a conveyer element 28c passing around and installed between these shafts, and a shape retaining mold 64. The shape retaining mold 64 comprises the upper and lower molds having the grooves formed to fit the shape of the bag, for example.

The extruded tube 24 is conveyed in a state that is held horizontally by the shape retaining mold 64. Also, the shape retaining mold 64 is moved to a specific position at the same speed as the conveyer 28 while retaining the extruded tube 24, for example. Then an arrangement is made so that when the mold arrives at such a specific position, the upper and lower molds are opened, and then, the die is returned to the original position. In this respect, the shape retaining mold 64 and the conveyer 28 are independent of each other, and are arranged so as not to interfere with each other in the vertical direction.

Although the medical fluid is supplied to the interior of the extruded tube 24 from the nozzle 26a of the medical fluid supply line 26, the extruded tube 24 is held by the shape retaining mold 64. Since the tube is thus maintained in a given shape, it is possible to fill the medical fluid in each of the chambers uniformly.

The fluid passages of the extruded tube 24 conveyed by the shape retaining mold 64 are sealed by the welding and cutting device 57, and, at the same time, the fused portions 24a are cut. A sealer and a cutter may be arranged separately.

In this respect, the shape retaining mold 64 may be adopted for the embodiment described in conjunction with FIG. 3.

The other descriptions for each of the manufacturing processes described in conjunction with FIG. 17 to FIG. 20 are the same as those given in conjunction with FIGS. 1 to FIG. 12. Here, therefore, these descriptions are omitted here.

FIG. 21 is a view schematically showing the system comprising the device for supplying the sterile air, the device for recovering the air, the device for supplying the medical fluid and the safety device. The device for supplying the sterile air includes a first sterile air supply line 25 and a second sterile air supply line 26b. Suction pumps 51 and 50, heaters 49 and 48, valves 55 and 54, air filters 46 and 45 are arranged in each of these air supply lines. The air, e.g. the outside air, drawn into the system by the suction pumps 51 and 50 is heated by the heaters 49 and 48° to 200° C., for example, and then, after the dust is removed by the air filters 46 and 45, the air is supplied to the interior of the extruded tube 24. The air supply pressure can be adjusted by the suction pumps 51 and 50 and the valves 55 and 54.

A valve 56 and an air filter 47 are arranged in the air recovering line 27 of the device for collecting the air. The air in the extruded tube 24 is forced into the air recovering line 27 by the interior pressure of the tube, and, after the volatile component and others contained in the recovered air are removed by the air filter 47 through the valve 56, the air is released to the outside air or a recovering tank.

The device for supplying the medical fluid comprises a medical fluid tank 52, a dissolving tank 65, distilling tank (distilling column) 61 connected to the dissolving tank 65 and a solute tank 60 for storing the solute of the medical fluid. The medical fluid supply line 26 is connected to the medical fluid tank 52. The valve 53 and the filter 63 for removing bacteria are arranged in the middle of the medical fluid supply line 26. Also, the medical fluid tank 52 and the dissolving tank 65 are connected by the line 69 for conducting the medical fluid and the valve 67 in line 69. Further, the dissolving tank 65 is connected to a switching valve 66 arranged in the middle of the second sterile air supply line 26b by the line 68 for conducting the sterile air.

The solute is fed from the tank 60 for the solute to the dissolving tank 65. A distilled water heated to a temperature of approximately 80° C. is fed from the distilling tank 61. The solute and the distilled water are measured and mixed in the dissolving tank 65. The sterile air is fed to the dissolving tank 65 from the second sterile air supply line 26b by switching the switch valve 66 to connect the line 68 for introducing the sterile air to the air supply line 26b.

The medical fluid in the tank 65 is under the pressure of the sterile air, and, when the valve 67 is released, the medical fluid is supplied to the medical fluid tank 52 through the line 69 for conducting medical fluid, and temporarily stored in it.

The medical fluid in the medical fluid tank 52 is fed through the medical fluid supply line 26 via the valve 53 into the extruded tube 24 and the filter 63 for removing bacteria. In this respect, the flow rate adjustment (open and close adjustment) of each of the valves 53, 54, 55, 56, 66 and 67 is performed by a controller 59.

The safety device is arranged so that when a sensor 58 for detecting liquid leakage, which is arranged on the receiving side of the horizontal carrier 62, detects any liquid leakage from the extruded tube 24 mounted on the horizontal conveyor 62, it causes the controller 59 to close each of the above-mentioned valves 53, 54, 55, 56, 66, and 67 in order to shut off each of the lines 25, 26b, 26, 27, 68 and 69. At the same time, the operation of the extruding machine 21, device 23a for supplying outlet devices, device 23 for forming the extruded tube, horizontal conveyor 62, and others are suspended.

Also, the above-mentioned welding and cutting device 57 seals the fluid passages of the fused portions of the extruded tube 24 to block the flow of the medical fluid in the extruded tube 24. In this state, it is possible to prevent bacteria and others in the outside air from entering and being mixed with the solution in the die 22 and extruded tube 24. The sensor 58 can be installed arbitrarily at any place along the horizontal carrier 62.

The above-mentioned device for supplying the sterile air, device for recovering the air, device for supply the medical fluid and safety device may also be applicable to the apparatus for manufacturing the bags shown in FIGS. 7 and 17.

According to the above-mentioned embodiments, it is possible to obtain aseptic conditions in the manufacturing processes of the bags for medical use for the reasons given below.

(1) Sterile material

The die 22 is always maintained at a temperature of 200° C. in operation. Therefore, even if the material is put in the hopper 21a, all the bacteria are killed in the vicinity of the die 22. Also, during the period from the installation of the die 22 to the start of operation, the extruding machine 21 is test run for a given period of time until the temperature inside the die 22 becomes 200° C. As a result, bacteria in the extruding machine 21 and the die 22 are all killed.

(2) Sterile medical fluid

The distilled water which is heated to a temperature of 80° C. in the distilled water tank 61 is mixed with the solute in the medical fluid tank 52. This mixture is further passed through the filter 63 for removing bacteria, and then, injected into the extruded tube 24. Therefore, the sterility of the medical fluid can be maintained.

(3) Sterile air supply

The air supplied to the interior of the extruded tube 24 is heated by the heaters 48 and 49 to a temperature of 200° C. At the same time, the air is supplied through the filters 45 and 46 for removing bacteria. Therefore, the sterility of the supplied air can be maintained.

(4) To maintain sterile conditions, when an accidental liquid leakage from the tube 24 is detected by the liquid leakage sensor 58, each of the valves 53, 54, 55, 56, 66, and 67 for the lines of the sterile air supply device, air recovering device and medical fluid supply device is closed. Then, the fluid passages of the fused portions of the extruded tube 24 are blocked or sealed by the welding and cutting device 57 in order to shut off the passages in the aforesaid devices as well as the interior of the extruded tube 24 from the outside air, thus making it possible to maintain sterile conditions, even when this type of accident occurs.

The excellent features of the present invention set forth above are listed below.

(1) From the extrusion of the composition material for the bags for medical use to the final process step, the portions forming the inner surface of the bags for medical use and the medical fluid to be filled are not exposed to the outside air. The bags for medical use can be manufactured in sterile and dustless conditions.

(2) While maintaining the medical fluid in a sterile condition, the material for the bags for medical use can be extruded and formed, and, at the same time, the medical fluid can be filled. The manufacturing processes can be maintained hygienically and significantly simplified, making it possible to manufacture the bags in a large quantity, e.g. as many as 100 or 200 units.

(3) In the device for forming the extruded tube, the fused portions are formed by pressing the extruded tube at a high temperature, and then, the narrow passages which are formed in the fused portions are sealed in the post-process. Therefore, compared to a method in which the entire apertures or openings on both ends of the tube are sealed or welded, the power consumption of the high frequency welder and other such devices becomes smaller, thus improving the economy of the manufacture.

(4) The additives contained in the component material for the extruded tube are recovered by the air recovering line. Thus no additives remain in the tube, contributing further to the maintenance of the hygienic condition.

(5) Since the outlet devices are welded at a high temperature to the extruded tube in the fused state, it is possible to install them simply and firmly. Also, by forcing the piercing needle through the outer surface of the bag, the medical fluid can be withdrawn from it. Furthermore, the outlet devices can be manufactured in a process independent of the bag main body, making it possible to use the particular outlet device which can best fits the size of the needle to be used.

What is claimed is:

1. A method of making bags for medical use comprising the steps of:
   a) forming an extruded tube in a fused state from a material for bags for medical use by extrusion;
   b) heating a plurality of outlet devices for the bags to form heated outlet devices;
   c) contacting the heated outlet devices to an outer surface of the extruded tube formed in step a) in the fused state to weld the outlet devices to the extruded tube;
   d) pressing said extruded tube in the fused state at intervals in a longitudinal direction along said extruded tube to form a plurality of fused portions spaced from each other in the longitudinal direction along the extruded tube, each of said fused portions having a fluid passage therethrough, to form chambers for a medical fluid in said extruded tube partitioned from each other by said fused portions;
   e) feeding a medical fluid into the chambers for the medical fluid through said fluid passages;
   f) sealing the fluid passages in the fused portions of the extruded tube in an air-tight manner after said feeding of step e); and
   g) cutting through each of said fused portions across a width direction of the extruded tube to form the bags for medical use filled with said medical fluid under sterile and dustless conditions.

2. A method according to claim 1, wherein each of said fused portions is formed after one of said heated outlet devices is welded to said extruded tube by rotating a single roller, said roller being provided with means for pressing the extruded tube to form said fused portions and means for installing said outlet devices on said extruded tube so that said extruded tube formed using said roller has a plurality of sections, each of said sections containing only one of said outlet devices and being bounded by two of said fused portions at opposite ends thereof.

3. A method according to claim 1, wherein said cutting step is performed after said sealing step.

4. A method according to claim 1, wherein said cutting step and said sealing step are performed simultaneously.

5. A method according to claim 1, wherein said step of feeding said a medical fluid comprises injecting the medical fluid through a medical fluid supply line extending into an interior of the extruded tube.

6. A method according to claim 1, further comprising supplying a sterile air into an interior of the extruded tube to maintain a shape of said extruded tube, and, at the same time, recovering air from the interior of the extruded tube containing a volatile component formed during the forming of said extruded tube.

7. An apparatus for manufacturing bags for medical use comprising:
   means for forming an extruded tube in a fused state from a material for bags for medical use by extrusion;
   means for heating a plurality of outlet devices for the bags to form heated outlet devices;
   means for contacting the heated outlet devices to an outer surface of the extruded tube in the fused state to weld the outlet devices to the extruded tube;
   means for pressing said extruded tube in the fused state at intervals in a longitudinal direction along said extruded tube to form a plurality of fused portions spaced from each other in the longitudinal direction along the extruded tube, each of said fused portions having a fluid passage therethrough, to form chambers for a medical fluid in said extruded tube partitioned from each other by said fused portions;
   means for feeding a medical fluid into the chambers for the medical fluid through said fluid passages;
   means for sealing the fluid passages in the fused portions of the extruded tube in an air-tight manner after said feeding of said medical fluid; and
   means for cutting through each of said fused portions across a width direction of the extruded tube to form the bags for medical use filled with said medical fluid under sterile and dustless conditions.

8. An apparatus according to claim 7, further comprising means for supplying a sterile air into an interior of the extruded tube and means for recovering air containing a volatile component from the interior of said extruded tube.

9. An apparatus according to claim 8, further comprising means for conveying horizontally the extruded tube delivered from said means for forming the extruded tube, and wherein said means for sealing and said means for cutting said fused portions are positioned adjacent said means for conveying the extruded tube horizontally.

10. An apparatus according to claim 9, further comprising means for detecting a liquid leakage of the medical fluid from the extruded tube positioned adjacent the means for conveying the extruded tube horizontally, said means for detecting producing a detection signal when said liquid leakage is detected; means for controlling said means for supplying the medical fluid, said means for supplying the sterile air and said means for recovering said air containing said volatile component in accordance with the detection signal received from said means for detecting liquid leakage to shut off said means for supplying the medical fluid, the means for supplying the sterile air and the means for recovering when the detection signal is received by said means for controlling; and means for safety control to enable said means for sealing and said means for cutting said fused portions to close the fluid passages of the fused portions of the extruded tube in an air-tight manner.

11. An apparatus according to claim 8, further comprising another means for supplying a sterile air to said extruded tube, said other means for supplying said sterile air to said extruded tube injecting the sterile air into the chambers formed in the extruded tube.

12. An apparatus according to claim 7, wherein said means for forming the extruded tube comprises an endless conveyer having rollers for pressing said extruded tube to form said fused portions.

13. An apparatus according to claim 7, wherein means for forming the extruded tube comprising rollers having a tube pressuring portion and a outlet device installing portion.

14. An apparatus according to claim 8, wherein said means for forming the extruded tube has a die and said means for supplying the medical fluid comprises a medical fluid supply line having a nozzle positioned in an interior of the extruded tube and extending through said die and a flow rate adjustment valve and a filter for removing bacteria arranged in said medical fluid supply line, a medical fluid reservoir tank connected to said medical fluid tank, a dissolving tank connected to said medical fluid tank, a tank for supplying a solute connected to said dissolving tank, and a tank for supplying a distilled water connected to said dissolving tank, and means for supplying a sterile air connected to said dissolving tank.

15. An apparatus according to claim 14, further comprising another sterile air supply line having a nozzle and extending through the interior of said medical fluid supply line, and wherein the nozzle for said other sterile air supply line is extended from the nozzle of said medical fluid supply line.

16. An apparatus according to claim 15, wherein said means for supplying the sterile air to the extruded tube comprises a sterile air supply line whose nozzle is extended into the interior of the extruded tube, a suction pump for introducing the air into said supply line, a heating device to heat said introduced air, and a filter for removing dust from said introduced air.

17. An apparatus according to claim 15, wherein the other sterile air supply line includes a suction pump for feeding the sterile air into the other sterile air supply line, heating means for heating the sterile air fed through the other sterile air supply line and filter means for removing dust from said sterile air fed through said other sterile air supply line.

18. An apparatus according to claim 17, wherein said other sterile air supply line has a switching valve for connecting and disconnecting the dissolving tank to the other sterile air supply line.

19. An apparatus according to claim 7, wherein means for heating said outlet devices comprises a hot plate for conveying the outlet devices in the direction of the extruded tube, and said hot plate has heating means for a portion of the outlet devices which are welded to the outer surface of the extruded tube in the fused state.

20. An apparatus according to claim 9, wherein said means for conveying the extruded tube horizontally has a shape retaining die to maintain a shape of the extruded tube.

* * * * *